(12) United States Patent
Vogel et al.

(10) Patent No.: US 10,772,748 B2
(45) Date of Patent: *Sep. 15, 2020

(54) STENT (71) Applicant: Covidien LP, Mansfield, MA (US)

(72) Inventors: Jeffrey H Vogel, Brooklyn Park, MN (US); Paul Noffke, St. Paul, MN (US); Ram Balachandran, Maple Grove, MN (US)

(73) Assignee: COVIDIEN LP, Mansfield, MA (US)

( * ) Notice: Subject to any disclaimer, the term of this patent is extended or adjusted under 35 U.S.C. 154(b) by 137 days.

This patent is subject to a terminal disclaimer.

(21) Appl. No.: 15/918,912

(22) Filed: Mar. 12, 2018

(65) Prior Publication Data

US 2018/0200090 A1    Jul. 19, 2018

Related U.S. Application Data

(60) Division of application No. 14/993,734, filed on Jan. 12, 2016, now Pat. No. 9,943,425, which is a continuation of application No. 13/834,713, filed on Mar. 15, 2013, now Pat. No. 9,259,335.

(51) Int. Cl.
*A61F 2/91* (2013.01)
*A61F 2/89* (2013.01)
*A61F 2/82* (2013.01)
*A61F 2/915* (2013.01)

(52) U.S. Cl.
CPC .................. *A61F 2/89* (2013.01); *A61F 2/82* (2013.01); *A61F 2/915* (2013.01); *A61F 2002/91508* (2013.01); *A61F 2002/91516* (2013.01); *A61F 2002/91575* (2013.01)

(58) Field of Classification Search
CPC ...... A61F 2/89; A61F 2/91; A61F 2/07; A61F 2/915; A61F 2002/91575; A61F 2002/91558; A61F 2002/91533

See application file for complete search history.

(56) References Cited

U.S. PATENT DOCUMENTS

| 4,733,665 A * | 3/1988 | Palmaz .................. A61F 2/915 606/108 |
| 5,449,373 A | 9/1995 | Pinchasik et al. |
| 5,707,386 A | 1/1998 | Schnepp-Pesch et al. |

(Continued)

FOREIGN PATENT DOCUMENTS

| CN | 1479596 | 3/2004 |
| CN | 101385669 | 3/2009 |

(Continued)

OTHER PUBLICATIONS

Response to Examination Report dated Feb. 22, 2018, from counterpart European Application No. 14709048.4, filed Jun. 25, 2018, 8 pp.

(Continued)

*Primary Examiner* — Vi X Nguyen
(74) *Attorney, Agent, or Firm* — Shumaker & Sieffert, P.A.

(57) ABSTRACT

A stent comprising a stent body and a plurality of cells is disclosed. The stent body defines a length. Each cell includes two structural members extending in an undulating pattern. Each structural member includes a plurality of cell segments defining a plurality of nodes therebetween. At least one node includes a non-constant radius of curvature.

14 Claims, 6 Drawing Sheets

(56) References Cited

U.S. PATENT DOCUMENTS

| | | | |
|---|---|---|---|
| 5,718,713 A | 2/1998 | Frantzen | |
| 5,759,192 A | 6/1998 | Saunders | |
| 5,843,164 A | 12/1998 | Frantzen et al. | |
| 5,860,999 A | 1/1999 | Schnepp-Pesch et al. | |
| 5,965,516 A | 10/1999 | Boutique et al. | |
| 6,190,406 B1 | 2/2001 | Duerig et al. | |
| 6,306,141 B1 | 10/2001 | Jervis | |
| 6,348,065 B1 | 2/2002 | Brown et al. | |
| 6,358,274 B1 | 3/2002 | Thompson | |
| 6,558,415 B2 | 5/2003 | Thompson | |
| 6,623,518 B2 | 9/2003 | Thompson et al. | |
| 6,699,278 B2 | 3/2004 | Fischell et al. | |
| 6,755,856 B2 | 6/2004 | Flerens et al. | |
| 6,814,746 B2 | 11/2004 | Thompson et al. | |
| 6,818,014 B2 | 11/2004 | Brown et al. | |
| 6,863,685 B2 | 3/2005 | Davila et al. | |
| 6,913,619 B2 | 7/2005 | Brown et al. | |
| 6,962,603 B1 | 11/2005 | Brown et al. | |
| 6,981,986 B1 | 1/2006 | Brown et al. | |
| 7,147,660 B2 | 12/2006 | Chobotov et al. | |
| 7,147,661 B2 | 12/2006 | Chobotov et al. | |
| 7,316,711 B2 * | 1/2008 | Allen | A61F 2/91 623/1.15 |
| 7,329,277 B2 | 2/2008 | Addonizio et al. | |
| 7,473,275 B2 | 1/2009 | Marquez | |
| 7,625,400 B2 | 12/2009 | Bowe et al. | |
| 7,655,033 B2 | 2/2010 | Fearnot et al. | |
| 7,753,948 B2 | 7/2010 | Roeder et al. | |
| 7,766,954 B2 | 8/2010 | Chobotov et al. | |
| 7,993,388 B2 | 8/2011 | Lee et al. | |
| 8,114,149 B2 | 2/2012 | Fishcell et al. | |
| 8,167,927 B2 | 5/2012 | Chobotov | |
| 8,187,396 B2 | 5/2012 | Parker | |
| 8,211,162 B2 | 7/2012 | Tischler et al. | |
| 8,236,043 B2 | 8/2012 | Caro et al. | |
| 8,241,346 B2 | 8/2012 | Chobotov | |
| 8,328,864 B2 | 11/2012 | Niermann | |
| 8,382,816 B2 | 2/2013 | Pollock et al. | |
| 8,658,081 B2 | 2/2014 | Gale et al. | |
| 9,180,031 B2 | 11/2015 | Vogel et al. | |
| 9,259,335 B2 | 2/2016 | Vogel et al. | |
| 9,943,425 B2 | 4/2018 | Vogel et al. | |
| 2002/0007212 A1 | 1/2002 | Brown et al. | |
| 2004/0093073 A1 | 5/2004 | Lowe et al. | |
| 2004/0167635 A1 | 8/2004 | Yachia et al. | |
| 2005/0096727 A1 | 5/2005 | Allen et al. | |
| 2006/0015173 A1 | 1/2006 | Clifford | |
| 2007/0100434 A1 | 5/2007 | Gregorich et al. | |
| 2007/0239263 A1 | 10/2007 | Fliedner | |
| 2008/0221661 A1 | 9/2008 | Bidne et al. | |
| 2009/0105809 A1 | 4/2009 | Lee et al. | |
| 2010/0137974 A1 | 6/2010 | Chouinard et al. | |
| 2010/0262227 A1 | 10/2010 | Rangwala et al. | |
| 2010/0312326 A1 | 12/2010 | Chuter et al. | |
| 2011/0213455 A1 | 9/2011 | Obradovic et al. | |
| 2012/0165920 A1 | 6/2012 | Meyer et al. | |
| 2012/0226346 A1 | 9/2012 | Boismier et al. | |
| 2013/0218260 A1 | 8/2013 | Schlun et al. | |
| 2014/0128959 A1 | 5/2014 | Gale et al. | |
| 2015/0105852 A1 | 4/2015 | Noffke et al. | |
| 2018/0296376 A1 | 10/2018 | Vogel et al. | |

FOREIGN PATENT DOCUMENTS

| | | |
|---|---|---|
| CN | 101516291 | 8/2009 |
| CN | 100566681 | 12/2009 |
| DE | 10144430 | 3/2003 |
| EP | 1523959 | 4/2005 |
| WO | WO97/025937 | 7/1997 |
| WO | WO 2002100298 | 12/2002 |
| WO | WO2003017870 | 3/2003 |
| WO | WO2004028571 | 4/2004 |
| WO | WO2007/005800 | 1/2007 |
| WO | WO2007013102 | 2/2007 |
| WO | WO2008/005535 | 1/2008 |
| WO | 2012091770 A1 | 7/2012 |
| WO | WO2012/096716 | 7/2012 |
| WO | WO2012/143731 | 10/2012 |

OTHER PUBLICATIONS

Notice of Allowance from U.S. Appl. No. 14/878,600, dated Mar. 21, 2018, 8 pp.
Decision on Appeal from U.S. Appl. No. 14/055,120, dated Feb. 19, 2019, 23 pp.
Office Action from U.S. Appl. No. 14/055,120, dated May 16, 2019, 19 pp.
Final Office Action from U.S. Appl. No. 14/055,120, dated Jul. 14, 2016, 16pp.
First Office Action, and translation thereof, from counterpart Chinese Application No. 201480015518.0. dated Aug. 25, 2016.
Notice of Appeal and Pre-Appeal Brief Request for Review from U.S. Appl. No. 14/055,120, filed Oct. 14, 2016, 7 pp.
Second Office Action, and translation thereof, from counterpart Chinese Application No. 201480015518.0. dated Apr. 10, 2017, 10 pp.
Examiners Answer from U.S. Appl. No. 14/055,120, dated May 5, 2017, 21 pp.
Final Rejection from U.S. Appl. No. 14/878,600, dated May 12, 2017, 12 pp.
Response to Examiner's Answer dated May 5, 2017, from U.S. Appl. No. 14/055,120, filed Jul. 5, 2017, 16 pp.
Prosecution History from U.S. Appl. No. 14/055,120, dated May 8, 2015, through Jun. 8, 2016, 91 pp.
U.S. Appl. No. 14/878,600 by Jeffrey H. Vogel et al., filed Oct. 8, 2015.
Prosecution History from U.S. Appl. No. 13/834,840, dated Sep. 12, 2014 through Aug. 31, 2015, 63 pp.
Prosecution History from U.S. Appl. No. 13/834,713, dated Mar. 12, 2015, through Dec. 16, 2015, 30 pp.
Office Action from U.S. Appl. No. 14/878,600, dated Dec. 6, 2016, 10 pp.
Response to Office Action dated Dec. 6, 2016, from U.S. Appl. No. 14/878,600, filed Mar. 6, 2017, 11 pp.
Office Action from U.S. Appl. No. 14/055,120, dated Jun. 1, 2015 15pp.
Final Office Action from U.S. Appl. No. 14/055,120, dated Oct. 16, 2015 13 pp.
Notice of Allowance from U.S. Appl. No. 13/834,840, dated Apr. 3, 2015, 7pp.
Final Office Action from U.S. Appl. No. 13/834,840, dated Jan. 16, 2015, 9 pp.
Non-Final Office Action from U.S. Appl. No. 13/834,840, dated Sep. 12, 2014, 13pp.
International Search Report for PCT Application Serial No. PCT/US2014/017095, dated Apr. 25, 2014, 4pgs.
International Search Report for PCT Application Serial No. PCT/US2014/017102, dated Jun. 16, 2014, 3pgs.
Office Action from U.S. Appl. No. 16/016,126, dated Jan. 13, 2020, 10 pp.
Response to Office Action dated Jan. 13, 2020, from U.S. Appl. No. 16/016,126, filed Apr. 9, 2020, 12 pp.
Notice of Allowance from U.S. Appl. No. 13/834,840, dated Jul. 10, 2015, 7 pp.
Prosecution History from U.S. Appl. No. 14/055,120, dated Mar. 10, 2015 through Jan. 29, 2020, 263 pp.
Prosecution History from U.S. Appl. No. 14/878,600, dated Oct. 12, 2015 through May 16, 2018, 89 pp.
Prosecution History from U.S. Appl. No. 14/993,734, dated Apr. 5, 2016 through Dec. 13, 2017, 42 pp.
Examination Report from counterpart European Application No. 14709048.4, dated Feb. 22, 2018, 6 pp.
Examination Report from counterpart European Application No. 14709048.4, dated Dec. 5, 2018, 4 pp.

(56) References Cited

OTHER PUBLICATIONS

Response to Examination Report dated Dec. 5, 2018, from counterpart European Application No. 14709048.4, filed Apr. 3, 2019, 10 pp.
Notice of Intent to Grant and Text Intended to Grant from counterpart European Application No. 14709048.4, dated Mar. 25, 2020, 31 pp.
International Preliminary Report on Patentability and Written Opinion of International Application No. PCT/US2014/017102, dated Sep. 15, 2015, 11 pp.
International Search Report from International Application No. PCT/US2014/017102, dated Sep. 25, 2014, 3 pp.
Written Opinion, and machine translation thereof, from counterpart Korean Application No. 10-2015-7028512, dated Apr. 24, 2020, 14 pp.
Notification to Grant, and translation thereof, from counterpart Chinese Application No. 201480015518.0, dated Sep. 13, 2017, 3 pp.
Response to Israel Office Action dated Feb. 6, 2019, from counterpart Israel Application No. 240782, filed May 20, 2019, 10 pp.
Final Office Action from U.S. Appl. No. 16/016,126, dated Jun. 18, 2020, 9 pp.

\* cited by examiner

STENT

This application is a divisional of U.S. patent application Ser. No. 14/993,734, filed Jan. 12, 2016 and naming inventors Vogel et al., which is a continuation of U.S. patent application Ser. No. 13/834,713, filed Mar. 15, 2013 and naming inventors Vogel et al., now U.S. Pat. No. 9,259,335. The entire content of each of these applications is incorporated herein by reference.

BACKGROUND

1. Technical Field

The present disclosure relates generally to stents, and, in particular, relates to stents having particular nodes with a non-constant radius of curvature.

2. Description of Related Art

Stents are widely used for numerous applications where the stent is placed in the lumen of a patient and expanded. Such stents may be used in coronary or other vasculature, as well as other body lumens.

Commonly, stents are cylindrical members. The stents expand from reduced diameters to enlarged diameters. Stents may either be self-expanding or balloon-expandable. Self-expanding stents are generally inserted into vasculature via a delivery device; the removal of the delivery device causes the stent to radially expand. Balloon-expandable stents are placed on a balloon catheter with the stent in the reduced-diameter state. So placed, the stent is advanced on the catheter to a placement site. At the site, the balloon is inflated to expand the stent to the enlarged diameter. The balloon is deflated and removed, leaving the enlarged diameter stent in place. So used, such stents are used to substantially retain or expand diameters of occluded sites within a patient's vasculature or other lumen.

Examples of stents are numerous. For example, U.S. Pat. No. 5,449,373 to Pinchasik et al. teaches a stent with at least two rigid segments joined by a flexible connector. U.S. Pat. No. 5,695,516 to Fischell teaches a stent with a cell having a butterfly shape when the stent is in a reduced-diameter state. Upon expansion of the stent, the cell assumes a hexagonal shape.

When stents are placed in certain parts of the body, it may be desirable for the stent to be both strong and flexible. For example, when a stent is placed within a patient's vasculature at or near a patient's joint (e.g., hip, knee, elbow, etc.), the stent may be bent often and may be subject to a relatively large amount of mechanical strain. Thus, a stent that is both flexible and strong may be desirable for use in these and other instances.

SUMMARY

The present disclosure relates to a stent comprising a stent body and a plurality of cells. Each cell includes two structural members extending in an undulating pattern. Each structural member includes a plurality of cell segments defining a plurality of nodes therebetween. At least one node includes a non-constant radius of curvature.

In disclosed embodiments, the at least one node that includes a non-constant radius of curvature includes at least two distinct radii of curvature.

In disclosed embodiments, a first node includes a radius of curvature of between about 0.0015 inches and about 0.0030 inches. Here, it is disclosed that a second node includes a radius of curvature of between about 0.0050 inches and about 0.0150 inches. Here, it is disclosed that a third node includes a radius of curvature of between about 0.0015 inches and about 0.0030 inches. Here, it is disclosed that a fourth node includes a radius of curvature of between about 0.0050 inches and about 0.0150 inches.

The present disclosure also relates to a stent comprising a stent body defining a length and comprising a plurality of cells. Each cell comprises two structural members extending in an undulating pattern. Each structural member comprises a plurality of cell segments defining a plurality of peaks and valleys therebetween. A first segment and a second segment define a first peak. The second segment and a third segment define a first valley. The third segment and a fourth segment define a second peak. The fourth segment and a fifth segment define a second valley. The fifth segment and a sixth segment define a third peak. At least one peak or valley includes a non-constant radius of curvature.

In disclosed embodiments, each of the first peak and the first valley include a non-constant radius of curvature.

In disclosed embodiments, the at least one peak or valley that includes a non-constant radius of curvature includes at least two distinct radii of curvature.

In disclosed embodiments, the each of the first peak and the first valley include at least two distinct radii of curvature.

In disclosed embodiments, the first peak includes a radius of curvature of between about 0.0015 inches and about 0.0030 inches. Here, it is disclosed that the second peak includes a radius of curvature of between about 0.0050 inches and about 0.0150 inches. Here, it is disclosed that the first valley includes a radius of curvature of between about 0.0015 inches and about 0.0030 inches. Here, it is disclosed that the second valley includes a radius of curvature of between about 0.0050 inches and about 0.0150 inches.

In disclosed embodiments, the second peak, the third peak and the second valley each include a single radius of curvature. Here, it is disclosed that the radius of curvature is between about 0.0001 inches and about 0.0020 inches.

In disclosed embodiments, the each structural member includes a seventh segment and an eighth segment. The sixth segment and the seventh segment define a third valley, and the seventh segment and the eighth segment define a fourth peak. Here, it is disclosed that the second peak, the third peak, the fourth peak, the second valley, and the third valley each include a single radius of curvature, and the radius of curvature is between about 0.0001 inches and about 0.0020 inches.

The present disclosure also relates to a stent comprising a stent body defining a length and comprising a plurality of cells. Each cell comprises two structural members extending in an undulating pattern. Each structural member comprising a plurality of cell segments defining a plurality of nodes therebetween. The radius of curvature of a first node is different from a radius of curvature of a second node. At least one node includes a non-constant radius of curvature.

In disclosed embodiments, the at least one node that includes a non-constant radius of curvature is a third node.

BRIEF DESCRIPTION OF THE DRAWINGS

Embodiments of the present disclosure will be readily appreciated by reference to the drawings wherein.

DESCRIPTION

In the following description, the terms "proximal" and "distal" as used herein refer to a direction or a position along a longitudinal axis of a catheter or medical instrument. The "proximal" or "trailing" end of the instrument is generally the segment of the instrument that is closest to the clinician or to the entrance site into a body. The "distal" or "leading" end of the instrument is generally the segment of the instrument placed farthest into a body lumen from the entrance site. Additionally, the term "preloaded" relates to the configuration of the stent prior to the stent being loaded into a catheter, and the term "predeployed" relates to the configuration of the stent while the stent is compacted into the catheter.

The stent of the present disclosure has particular application in the vasculature of a patient where it is subject to a relatively high amount of strain and movement. For example, the disclosed stent may be suitable for use within the vasculature of a patient's hip area, e.g., to help reduce problems associated with a deep vein thrombosis (DVT). However, the disclosed stent may be used in any interventional, diagnostic, and/or therapeutic procedure. The stent may be a component of an apparatus or system used in conjunction with any of the above applications.

The various embodiments of the disclosure will now be described in connection with the drawings. It should be understood that for purposes of better describing the disclosure, the drawings may not be to scale. Further, some of the figures may include enlarged or distorted portions for the purpose of showing features that would not otherwise be apparent.

Figure 1:
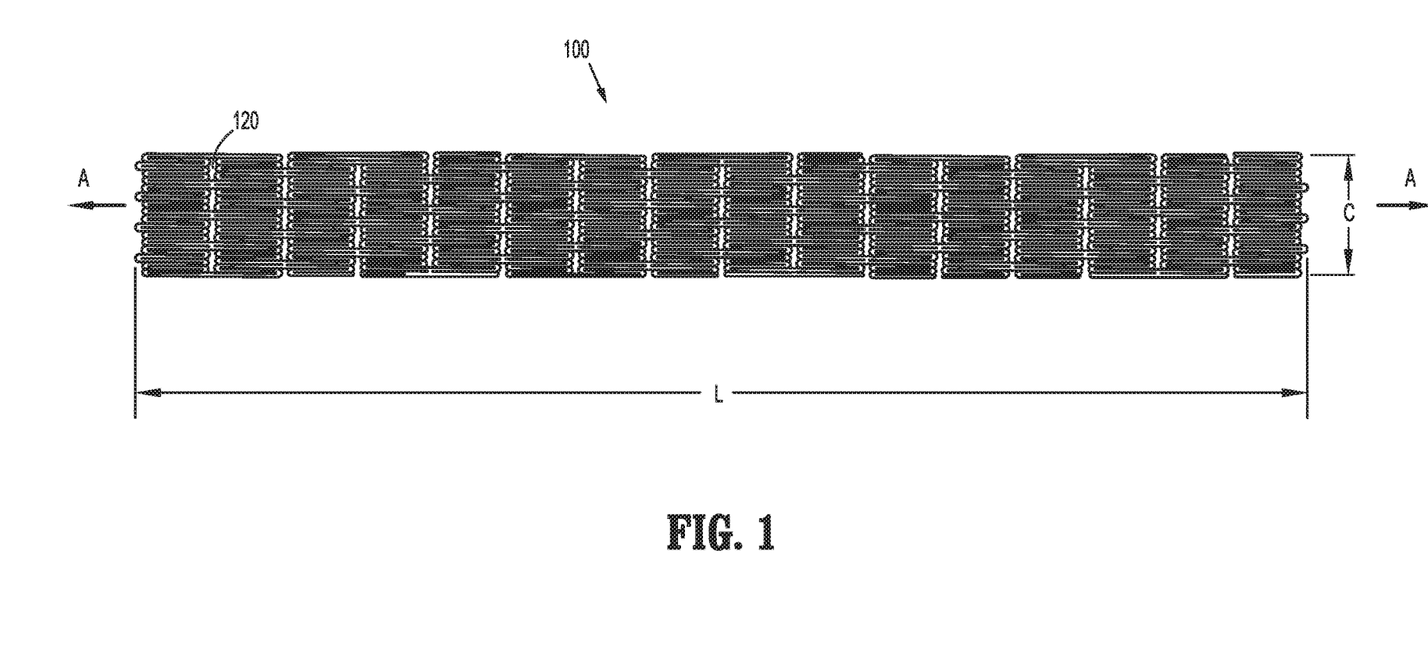
FIG. 1 is a plan view of a stent according to an embodiment of the present disclosure as it would appear if it were longitudinally split and laid out flat.
Figure 4:
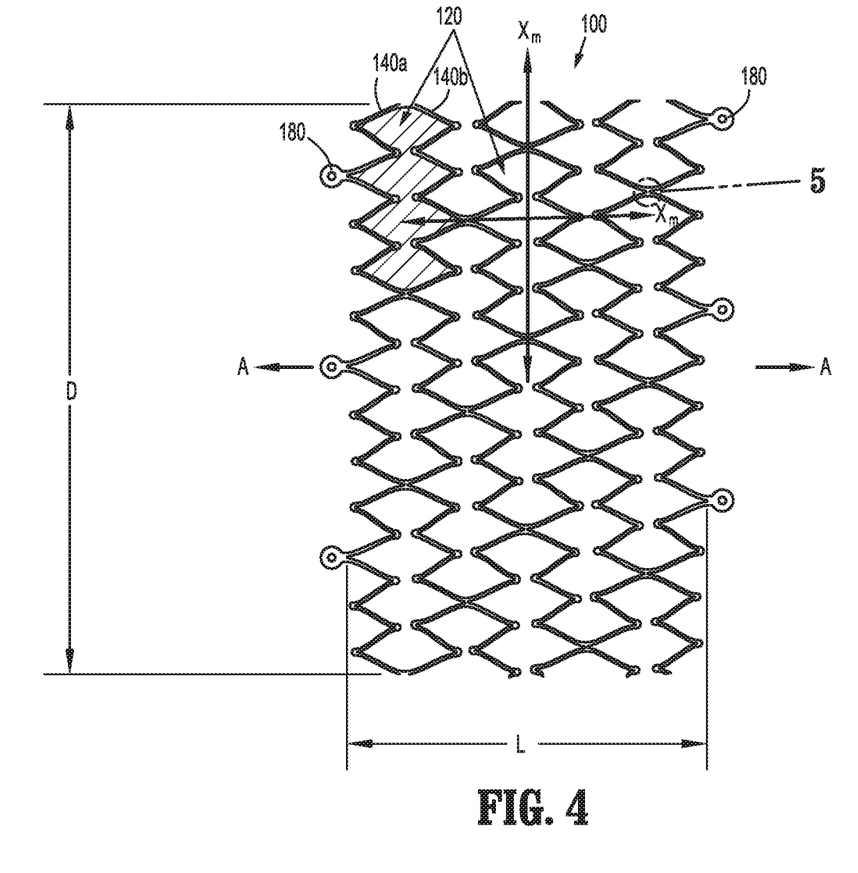
FIG. 4 is a plan view of a portion of the stent of FIG. 1 in a deployed/expanded orientation, the stent has been longitudinally cut and laid flat.

With initial reference to FIG. 1, the present disclosure includes a stent 100. Stent 100 may be expanded from a rest diameter (and a corresponding rest circumference C) to an expanded or enlarged diameter. While stent 100 is generally used when in a cylindrical configuration, for ease of illustration, FIG. 1 illustrates a stent 100 in a flattened condition. Moreover, FIG. 1 shows stent 100 cut longitudinally along its length L and laid flat, and is representative of the stent 100 after stent 100 has been laser cut from a shape-memory tube, for instance, but before stent 100 has been shape-set to the expanded diameter. FIG. 4 shows a portion of the stent 100 after the stent has been shape-set to the desired expanded diameter. In both FIGS. 1 and 4, the stent 100 is elongated along axis A-A and includes a stent body (i.e., a three-dimensional structure) having cell defining portions that define a plurality of cells 120, which are bounded areas which are open (i.e., extend through the wall thickness of the stent 100). After the stent 100 has been shape-set to the expanded diameter D as shown in FIG. 4, the cells 120 are generally more open than the cells depicted in FIG. 1.

With continued reference to FIG. 4, cells 120 have a longitudinal or major axis $X_M$-$X_M$ and a transverse or minor axis $X_m$-$X_m$; the major axis of the cell $X_M$-$X_M$ is perpendicular to the longitudinal axis A-A of stent 100. In disclosed embodiments, cell 120 may be repeated throughout a least a portion of the length L and the diameter D of the stent 100 (i.e., each cell 120 may be substantially identical to other cells 120).

Figure 2:
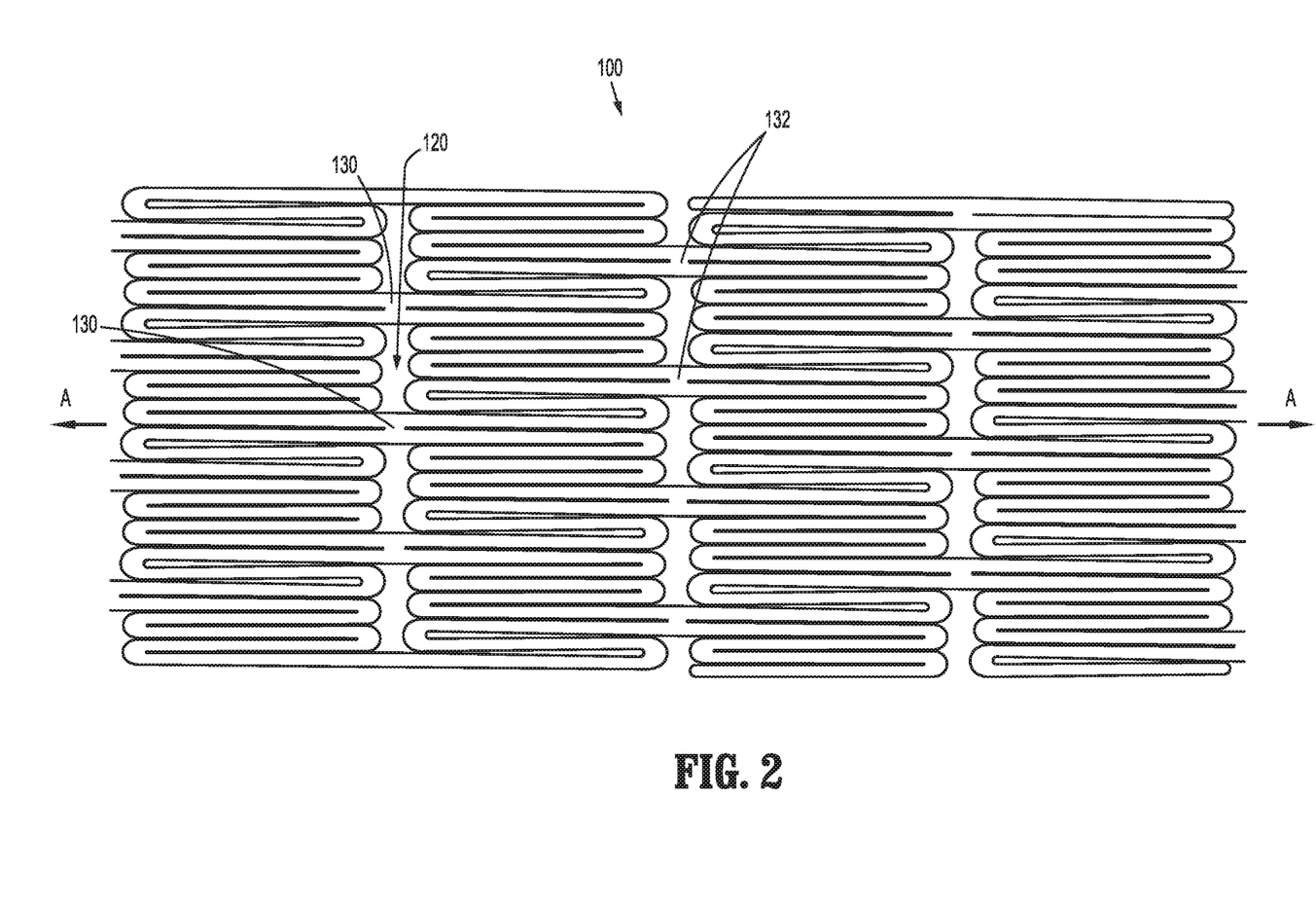
FIGS. 2 and 3 are enlarged views of portions of the stent of FIG. 1.
Figure 3:
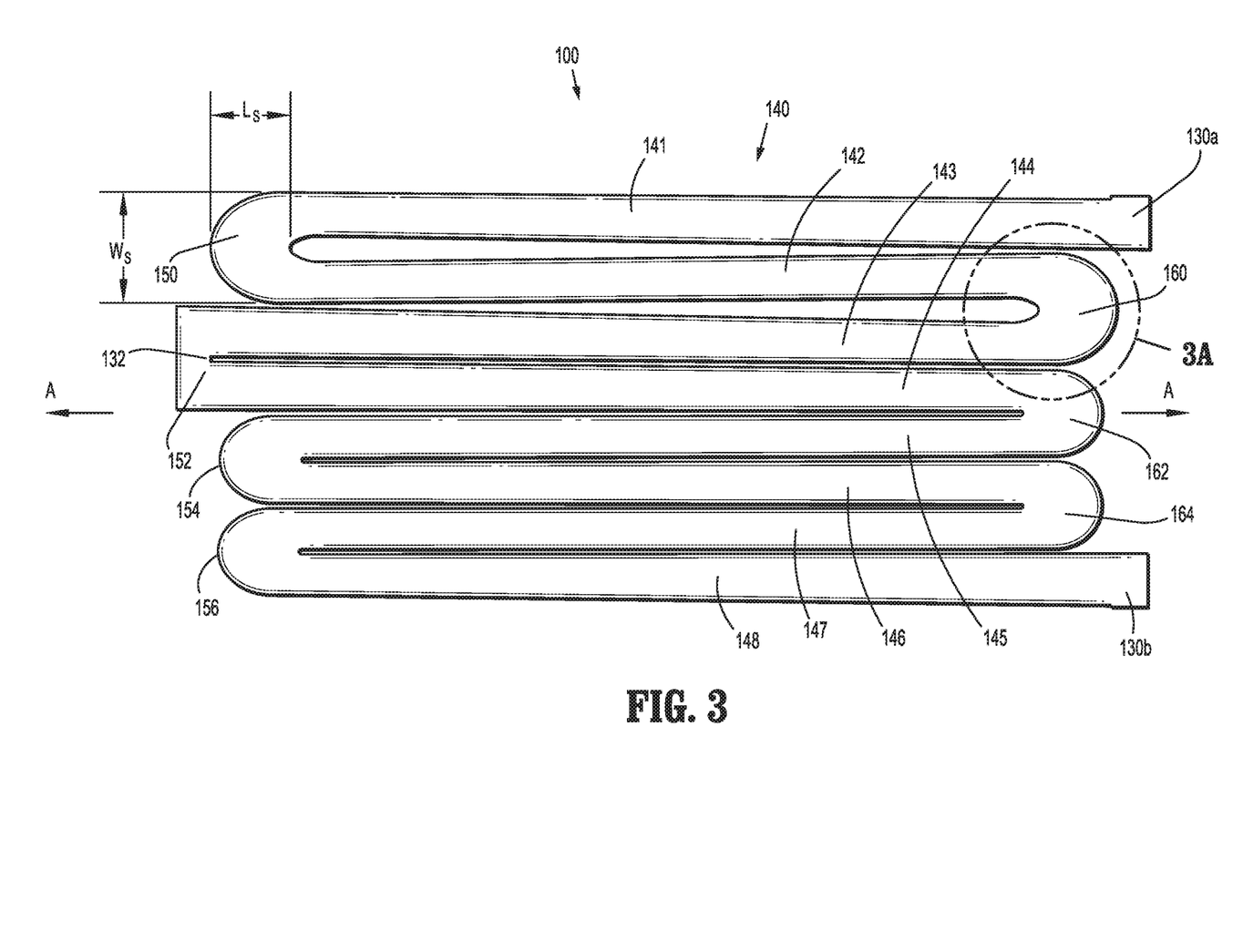

Referring to FIGS. 2 and 3, which are enlarged portions of the stent 100 of FIG. 1, the cell defining portions of stent 100 include first connection locations 130 and second connection locations 132. First and second connection locations are where circumferentially adjacent cell defining structures, as defined relative to axis A-A, are connected together, and where longitudinally adjacent cell defining portions, as defined relative to the axis A-A, are connected together.

With particular reference to FIG. 4, cells 120 are defined by portions of the tube material and include first and second longitudinal segments 140a and 140b, collectively referred to as cell segments 140. With additional reference to FIGS. 3 and 6, each of which illustrates half of a cell 120, each cell segment 140 has an undulating pattern which defines a plurality of peaks 150, 152, 154, 156 and valleys 160, 162, 164. The peaks 150, 152, 154, 156 are spaced outwardly or away from the longitudinal axis $X_M$-$X_M$, and the valleys 160, 162, 164 are spaced inwardly or toward the longitudinal axis $X_M$-$X_M$.

Figure 6:
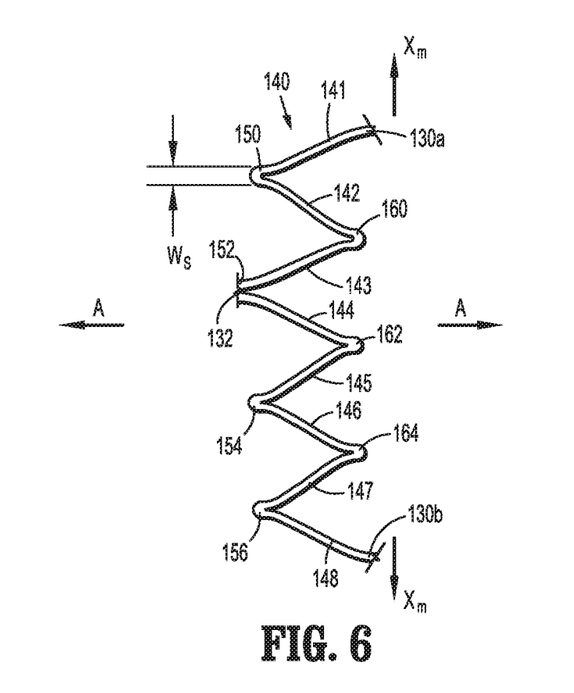

FIGS. 3 and 6 are enlarged portions of a stent illustrating certain aspects of a stent design that can be optimized based on the desired performance of the stent. FIGS. 3 and 6 illustrates a portion of a cell defining portion of stent 100, each cell segment 140 is shown including: 1) a first segment 141 that extends from a first connection location 130a to peak 150; 2) a second segment 142 that extends from peak 150 to valley 160; 3) a third segment 143 that extends from valley 160 to peak 152; 4) a fourth segment 144 that extends from peak 152 to valley 162; 5) a fifth segment 145 that extends from valley 162 to peak 154; 6) a sixth segment 146 that extends from peak 154 to valley 164; 7) a seventh segment 147 that extends from valley 164 to peak 156; and 8) an eighth segment 148 that extends from peak 156 to a second connection location 130b. It is additionally envisioned that first segment 141 and the last segment (e.g., sixth segment 146 or eighth segment 148) form a valley. Additionally, as shown in FIGS. 3 and 6, peak 152 is part of connection location 132. Collectively, peaks and valleys are referred to herein as nodes.

In the illustrated embodiment, segments 141-148 extend generally longitudinally along stent 100. The term "generally longitudinally" will be understood to mean that segments 141-148 are closer to a parallel relationship relative to the axis A-A of stent 100 (e.g., FIG. 3) than to a transverse relationship relative to the axis A-A of stent 100.

Each node is a generally semi-circular arcuate segment including at least one radius of curvature, a length "$L_S$" (along axis A-A), and a width "$W_S$" (perpendicular to axis A-A) (see FIG. 3). The radius of curvature is defined as the distance of the circular arc which best approximates the curve at that point, and is measured along an inside edge of the node, as shown in FIG. 3A.

Figure 3A:
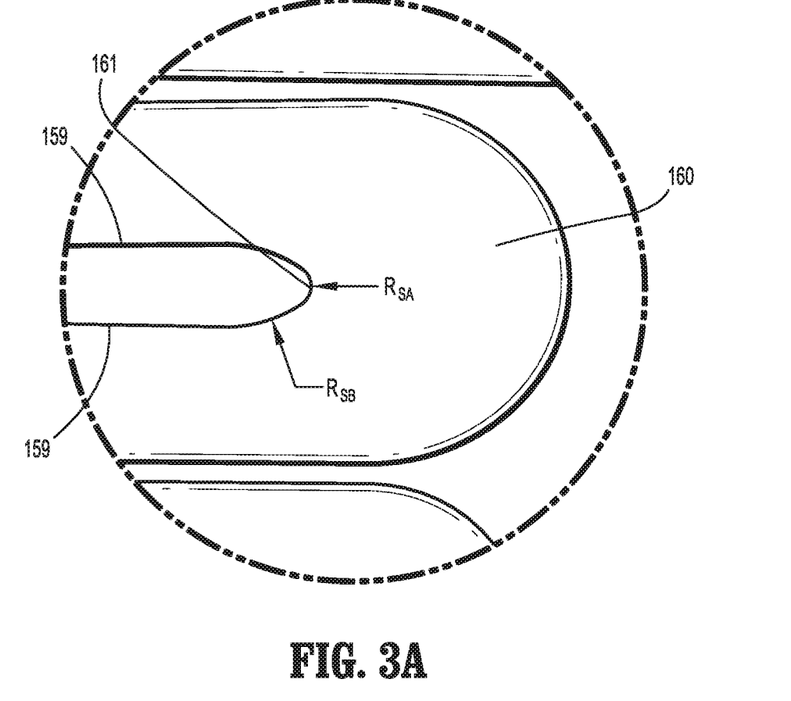
FIG. 3A is an enlarged view of a portion of the stent of FIG. 3.

With reference to FIGS. 3 and 3A, two nodes (i.e., peak 150 and valley 160) are shown having a non-constant radius of curvature as viewed along the inside edge of the node. Referring specifically to FIG. 3A, two different radii of curvature are shown and are indicated as "$R_{SA}$" and "$R_{SB}$." As shown, "$R_{SA}$" is the radius of curvature on the inner edge at the apex 161 of the valley 160, and "$R_{SB}$" is the radius of curvature on the inner edge of valley 160 located between the apex 161 and each relative flat portion 159 of segment 140. As illustrated, radius of curvature "$R_{SA}$" has a smaller value than radius of curvature "$R_{SB}$". Further, it is envisioned that radius of curvature "$R_{SA}$" is between about 0.0015 inches and about 0.0030 inches (e.g., equal to about 0.0020 inches), and that radius of curvature "$R_{SB}$" is between about 0.0050 inches and about 0.0150 inches (e.g., equal to about 0.0090 inches). It is further envisioned that the arc length of segment 140 along radius of curvature "$R_{SA}$" is between about 0.0020 inches and about 0.0070 (e.g., equal to about 0.0040 inches), and that the arc length of segment 140 along radius of curvature "$R_{SB}$" is between about 0.0020 inches and about 0.0080 inches (e.g., equal to about 0.0033 inches). Further, the transition between radius of curvatures "$R_{SA}$" and "$R_{SB}$" may be abrupt, smooth, and/or a combination thereof.

While FIG. 3A illustrates two radii, it is further envisioned that various nodes (e.g., peak 150 and valley 160) may include more than two radii of curvature associated therewith. Referring back to FIG. 3, the radii of curvature of each of nodes 152, 154, 156, 162 and 164 may be substantially constant and may be between about 0.0001 inches and about 0.0015 inches (e.g., equal to about 0.0010 inches). Moreover, the radii of curvature of each of nodes 150 and 160 may be equal or substantially equal to each other, and the radius of curvature of each of peak 152, valley 162, peak 154, valley 164, and peak 156 may be equal or substantially equal to each other.

Additionally, while particular nodes (i.e., peak 150 and valley 160) are each shown having a non-constant radius of curvature, it is envisioned and within the scope of the present disclosure that any combination of nodes 150, 152, 154, 156, 160, 162 and 164 may include a non-constant radius of curvature. It is further disclosed that any peak and any valley of each cell 120 may have any of the disclosed constant or non-constant radii of curvature.

The present disclosure also contemplates embodiments where nodes 152, 162, 156 and the valley created by segments 141 and 148 each include a non-constant radius of curvature. Here, it is envisioned that each of the non-constant radius of curvatures are equal to each other. In these embodiments, it is further envisioned that nodes 154 and 164 include a constant radius, which are equal to each other.

As discussed hereinabove, the disclosed stent 100 includes cells 120 having multiple nodes, wherein at least one node has a non-constant radius of curvature. It is envisioned that these features help improve the life and/or durability of the disclosed stent 100. For example, the mechanical strains undergone by stent 100 when stent 100 is within a patient's vasculature (e.g., within a region subject to repeated joint flexure) results in a more balanced distribution of strains versus a typical stent where each node has a constant and/or equal radius, for example. A combination of finite element analysis, durability testing, fatigue testing, and repeating bending load testing may be performed to help determine the desired ranges of dimensions for each node and to tune the desired performance of a given stent 100. For example, to help balance the strains undergone by stent, the portions of a radius of the node that experiences the highest strains during testing (e.g., finite element analysis, durability testing, fatigue testing, and/or repeating bending load testing) is increased. If/when a different node experiences the highest strains during a subsequent test, a portion of the radius of that node is increased. This testing process is repeated until the strength and/or size of the compacted diameter become unacceptable for its desired application, and/or until additional increases in node radius provides negligible additional improvement in strength or durability.

When stent 100 is compacted into the catheter (i.e., its predeployed configuration), the diameter of stent 100 is reduced as compared to when stent 100 has not yet been loaded into the catheter (i.e., its preloaded configuration). This associated reduction in stent circumference is accommodated by reduction in the angles between segments which results in an increase in bending strain (e.g., especially adjacent nodes). As the cell is deformed (e.g., when stent 100 is loaded into catheter, or when the delivery system is navigating through the vasculature to the treatment site), especially during bending or axial loading, certain angles between adjacent segments increase or decrease more than others due to the lack of symmetry inherent in most flexible stent designs. As a result, there is a greater amount of strain in the nodes that connect those adjacent segments. The amount of strain concentrated near the nodes can be calculated using finite element analysis, for example.

The maximum strain in a deformed stent is called the peak strain. The peak strain typically occurs in a single segment in the vicinity of a node although it may occur elsewhere in the stent depending on the stent design. Predominant strains in stents may be tensile (usually defined as positive) or compressive (usually defined as negative). Strains can be categorized as being of two kinds: normal strains and shear strains. Normal strains can be positive (e.g., tensile) or negative (e.g., compressive). There are positive and negative shear strains as well, but in this case the sign convention is arbitrary, and physically there is no real difference between positive and negative shear strains. Normal strains, which are also referred to as principal strains, are generally the basis for strain analysis and durability analysis of stents.

High tensile strains may cause cracks to initiate and propagate through the stent, leading to reduced fatigue life and stent fracture (i.e., failure mode). Compressive strains do not tend to cause cracks, and so generally do not cause reduced stent life unless the magnitude of the strain is extraordinary. Some portions of a deformed stent may be highly strained during use while other portions may not be strained at all. A deformed stent can be thought of as a collection of tiny volumetric regions, each region having a strain level; collectively, the strain levels of the regions range from a maximum negative value to a maximum positive value. For a stent in service in the body, if stent strains are maintained below the endurance limit of the stent material then high fatigue life may be expected assuming the stent material has undergone proper materials processing and surface finishing. However, if a stent in service in the body suffers stent strains above the endurance limit of the stent material then high fatigue life cannot be expected regardless of stent material processing and surface finishing.

Commonly, stents are designed such that the strain in the stent remains at a low level under pulsatile loading conditions, i.e. under oscillating circumferential compressive strains. However, it has been determined that stents implanted in other locations, for example within a patient's vasculature at or near a patient's joint, can subject a stent to larger amounts of strain than previously predicted.

Bending and any associated elongation of stent 100 results in concentration of tensile strains at and within particular nodes thereby exposing the segments near or adjacent the nodes, and the nodes themselves, to lower fatigue life. Concentration of compressive strains in other nodes permit the segments near or adjacent those nodes to sustain higher fatigue life. As such, balancing the strains experienced by the stent 100 increases the overall fatigue life of stent 100. Balancing the strain may involve changing the design of the stent 100 such that the nodes that are otherwise exposed to higher levels of tensile strains have a way to distribute that strain to help improve the fatigue life of the particular node and adjacent segments, and thus, help improve the fatigue life of the entire stent 100.

The design of stent 100 of the present disclosure helps balance the strain by providing nodes with a non-constant radius. As the strain is concentrated in regions where the radius of curvature is the smallest, it follows that by increasing the radius, the peak strain is reduced. The nodes having non-constant radii have a larger radius of curvature through the parts of the node that undergo the larger amount of strain, and a smaller radius of curvature through the parts of the node that undergo the smaller amount of strain. Thus, the portion of the node with the larger radius lowers the peak strain associated therewith, and which thus improves fatigue life (i.e., helps prevent the stent from breaking). Further, the nodes of stent 100 that include this non-constant radii of curvature may be the nodes that undergo the highest peak strains during various testing procedures. Therefore, the overall life and performance of the stent is improved.

However, while altering the radii of various nodes may improve certain aspects of the stent design, such changing of radii may affect the strength of at least part of the stent. More particularly, stent 100 may be compacted to a relatively small diameter in order to enable stent 100 to fit into a delivery system that travels through a patient's vasculature. Generally, as the node radius increases and the segment widths remain constant, the minimum compaction diameter increases in proportion to the increase in radius. If the required compaction diameter is desired to be a fixed amount, then as the node radius is increased, the segment widths would have to decrease. This decrease in segment width may lead to a decrease in stent strength. Thus, for each stent design and desired application, it is possible to tune the overall stent design to ensure the durability benefits outweigh the loss of strength or an increase in compaction diameter due to increasing the node radius. By way of a non-limiting example, for venous stents (as compared to arterial stents) the diameter of the delivery system may be less critical for two reasons: 1) veins generally have larger diameters than arteries; and 2) blood pressure is lower in veins versus arteries, so the size of an access hole made to get the delivery device into a vein may be less critical, as once the procedure is complete, it is easier to stop the bleeding from a hole in a vein than in an artery. Thus, the design of a stent can be tuned for a venous application by considering the desired strength of the stent, the desired durability, and the desired size of its compacted diameter, along with the interplay between these criteria.

It is further envisioned that in addition to stent 100 having at least node with a non-constant radius of curvature, at least two nodes of stent 100 include different radii of curvature from one another. In certain situations, a stent having a combination of nodes with different radii of curvature and with non-constant radii of curvature may further augment the balanced distribution of forces. Further details of stents having nodes with different radii of curvature from one another is disclosed in U.S. application Ser. No. 13/834,840, filed concurrently with the present application on Mar. 15, 2013, and granted on Nov. 10, 2015 as U.S. Pat. No. 9,180,031, the entirety of which is hereby incorporated by reference herein.

Figure 5:
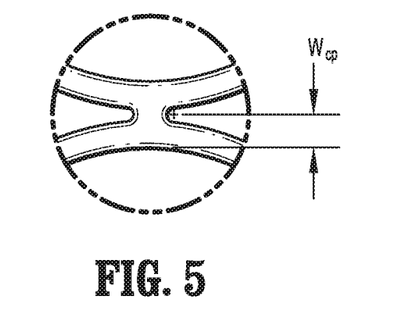
FIGS. 5 and 6 are enlarged views of portions of the stent shown in FIG. 4.

In disclosed embodiments, the width "$W_S$" of each node is between about 0.0240 inches and about 0.0265 inches (e.g., equal to about 0.0250 inches). In disclosed embodiments, the length "$L_S$" of each node is between about 0.0130 inches and about 0.0170 inches (e.g., equal to about 0.0155 inches). In disclosed embodiments, the width "$W_{CP}$" of connecting portions 130 (see FIG. 5) is between about 0.0100 inches and about 0.0200 inches (e.g., equal to about 0.0149 inches).

It is envisioned that the each cell 120 and the entire stent 100 can be of any reasonable dimension for the intended purpose of use within a patient's vasculature. Likewise, the total number of cells 120 can be of any reasonable value. Further, as shown in FIG. 4, connector members 180 may be included on stent 100 to temporarily secure stent 100 to a delivery device, for example.

In disclosed embodiments, the inside diameter of a pre-loaded stent 100 (i.e., prior to insertion into a catheter) is between about 0.5000 inches and about 0.6000 inches, and the inside diameter of a predeployed stent 100 (i.e., compacted within a catheter) is between about 0.0500 inches and about 0.0600 inches.

In use, stent 100 is advanced to a site in a bodily lumen. Stent 100 is then expanded at the site. Stent 100 may be expanded through any conventional means. For example, stent 100 may be placed on the balloon tip of a catheter. Here, the balloon is expanded at the site to generate radial forces on the interior of stent 100. The radial forces urge stent 100 to radially expand, e.g., without appreciable longitudinal expansion or contraction. Plastic deformation of the material of stent 100 (e.g., stainless steel) results in stent 100 retaining the expanded shape following subsequent deflation of the balloon.

Additionally, stent 100 can be mounted on a delivery catheter. As is conventionally known in the art, stent 100 can be held in a compressed orientation on the delivery catheter by a retractable sheath. As is also known in the art, the delivery catheter can be used to advance stent 100 to a deployment location (e.g., a constricted region of a vessel). At the deployment site, the sheath is retracted thereby releasing stent 100. Once released, stent 100 self-expands to the deployed diameter. While an envisioned use for the features disclosed in the accompanying figures relates to that of a self-expanding stent, the features also have benefits when used with non-self-expanding stents (e.g., balloon expandable stents made of a material such as stainless steel).

To advance to a site, the axis A-A of stent 100 must bend to navigate through a curved lumen. Further, for placement at a curved site in a lumen, stent 100 must be sufficiently flexible to retain a curved shape following expansion and to bend as the lumen bends over time.

Numerous modifications are possible. For example stent 100 may be lined with either an inner or outer sleeve (such as polyester fabric or ePTFE) to facilitate tissue growth. Also, at least a portion of stent 100 may include or be coated with radiopaque coatings such as platinum, gold, tungsten or tantalum. In addition to materials previously discussed, stent 100 may be formed of other materials, including, without limitation, MP35N, tantalum, platinum, gold, Elgiloy and Phynox. Alternatively, the stent 100 may be formed of a super-elastic or shape memory material (e.g., nitinol).

While three cells 120 are shown in FIG. 4 longitudinally connected along the diameter of stent 100, a different number of cells 120 could be so connected to vary the properties of stent 100 as a designer may elect. Likewise, while each column of cells 120 in FIG. 4 is shown as having three longitudinally connected cells 120, the number of longitudinally connected cells 120 could vary to adjust the properties of stent 100.

When forming stent 100 from a shape memory metal such as nitinol, stent 100 can be laser cut from a nitinol tube. Thereafter, stent 100 can be subjected to a shape-setting process in which the cut tube is expanded on a mandrel and then heated. Multiple expansion and heating cycles can be used to shape-set stent 100 to the final expanded diameter. It is envisioned that the final expanded diameter is equal to the desired deployed diameter of stent 100. During expansion, it is envisioned that stent 100 is axially restrained such that the length of stent 100 does not change during expansion. It is further envisioned that the finished stent 100 has an austenite finish temperature less than body temperature. Here, at body temperature, stent 100 will self-expand to the desired deployed diameter due to the shape memory characteristic of the metal forming stent 100.

From the foregoing and with reference to the various figure drawings, those skilled in the art will appreciate that certain modifications can also be made to the present disclosure without departing from the scope of the same. It is not intended that the disclosure be limited to the embodiments shown in the accompanying figures, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

The invention claimed is:

1. A stent comprising:
   a stent body defining a length and comprising a plurality of cells,
   wherein each cell comprises a first structural member and a second structural member each extending in an undulating pattern, and
   wherein the first structural member and the second structural member each comprises a plurality of cell segments defining a plurality of peaks and valleys therebetween,
   wherein the plurality of cell segments of the first structural member define a first peak including a first inner edge, a second peak including a second inner edge, a third peak including a third inner edge, and a fourth peak including a fourth inner edge,
   wherein at least one of the first inner edge, the second inner edge, the third inner edge, or the fourth inner edge defines a first radius of curvature that is non-constant,
   wherein another of the at least one of the first inner edge, the second inner edge, the third inner edge, or the fourth inner edge defines a second radius of curvature that is substantially constant, and
   wherein the second radius of curvature is less than the first radius of curvature.

2. The stent of claim 1, wherein the first inner edge, the second inner edge, and fourth inner edge each define the first radius of curvature that is non-constant, and the third inner edge defines the second radius of curvature that is substantially constant.

3. The stent of claim 2, wherein the second peak defines a connector location at which the first structural member connects to a circumferentially adjacent cell of the plurality of cells.

4. The stent of claim 2, wherein the plurality of cell segments of the second structural member define a first valley including a fifth inner edge, a second valley including a sixth inner edge, a third valley including a seventh inner edge, and a fourth valley including an eighth inner edge,
   wherein at least one of the fifth inner edge, the sixth inner edge, the seventh inner edge, or the eighth inner edge defines a third radius of curvature that is non-constant,
   wherein another of the at least one of the fifth inner edge, the sixth inner edge, the seventh inner edge, or the eighth inner edge defines a fourth radius of curvature that is substantially constant, and
   wherein the fourth radius of curvature is less than the third radius of curvature.

5. The stent of claim 4, wherein the first radius of curvature and the third radius of curvature are substantially equal.

6. The stent of claim 4, wherein the second radius of curvature and the fourth radius of curvature are substantially equal.

7. The stent of claim 4, wherein the first peak is circumferentially adjacent the first valley, the second peak is circumferentially adjacent the second valley, the third peak is circumferentially adjacent the third valley, and the fourth peak is circumferentially adjacent the fourth valley.

8. The stent of claim 7, wherein the first inner edge, the third inner edge, and fourth inner edge each define the third radius of curvature that is non-constant, and the second inner edge defines the fourth radius of curvature that is substantially constant.

9. The stent of claim 8, wherein the second valley defines a connector location at which the second structural member connects to another circumferentially adjacent cell of the plurality of cells.

10. The stent of claim 1, wherein the plurality of cell segments of the second structural member define a first valley including a fifth inner edge, a second valley including a sixth inner edge, a third valley including a seventh inner edge, and a fourth valley including an eighth inner edge,
    wherein at least one of the fifth inner edge, the sixth inner edge, the seventh inner edge, or the eighth inner edge defines a third radius of curvature that is non-constant,
    wherein another of the at least one of the fifth inner edge, the sixth inner edge, the seventh inner edge, or the eighth inner edge defines a fourth radius of curvature that is substantially constant, and
    wherein the fourth radius of curvature is less than the third radius of curvature.

11. The stent of claim 10, wherein the first radius of curvature and the third radius of curvature are substantially equal.

12. The stent of claim 10, wherein the second radius of curvature and the fourth radius of curvature are substantially equal.

13. The stent of claim 1, wherein the at least one of the first inner edge, the second inner edge, the third inner edge, or the fourth inner edge that defines that first radius of curvature that is non-constant includes at least two distinct radii of curvature, and wherein the at least two distinct radii of curvature are curved in a same direction.

14. The stent of claim 1, wherein the at least one of the first inner edge, the second inner edge, the third inner edge, or the fourth inner edge that defines that first radius of curvature that is non-constant includes:
    a first distinct radius of curvature at an apex of the at least one of the first inner edge, the second inner edge, the third inner edge, or the fourth inner edge that defines that first radius of curvature that is non-constant, and
    a second distinct radius of curvature located between the apex and each adjacent cell segment, wherein the first distinct radius of curvature is smaller than the second distinct radius of curvature.

* * * * *